United States Patent [19]

Clark et al.

[11] Patent Number: 4,671,728
[45] Date of Patent: Jun. 9, 1987

[54] HYDRAULIC SYSTEM FOR A MOBILE TRANSPORT VEHICLE THAT SUPPORTS AND POSITIONS A LOAD RELATIVE TO A DOCKING STRUCTURE

[75] Inventors: Ray Clark, Pewaukee; Frank M. Schmer, Jr., Greenfield, both of Wis.

[73] Assignee: Applied Power, Inc., Brookfield, Wis.

[21] Appl. No.: 754,022

[22] Filed: Jul. 11, 1985

[51] Int. Cl.⁴ .................. A61G 13/00; B65G 1/06
[52] U.S. Cl. .................................. 414/401; 5/63;
5/81 R; 5/424; 414/284; 414/663
[58] Field of Search ............... 180/2.1, 274; 269/322,
269/328; 5/63, 81 R, 81 B, 424, 86; 414/284,
663, 24.6, 279, 401

[56] References Cited

U.S. PATENT DOCUMENTS

| | | | |
|---|---|---|---|
| 3,519,150 | 7/1970 | Keenan et al. | 414/284 |
| 3,814,414 | 6/1974 | Chapa | 269/328 |
| 3,880,299 | 4/1975 | Zollinger et al. | 414/279 |
| 4,265,583 | 5/1981 | Baird et al. | 414/284 |
| 4,360,167 | 11/1982 | Beccalori et al. | 414/24.6 |

*Primary Examiner*—Lawrence J. Oresky
*Attorney, Agent, or Firm*—Andrus, Sceales, Starke & Sawall

[57] ABSTRACT

A hydraulic system for a mobile vehicle that supports and positions a load relative to a docking structure, such as a patient relative to a medical diagnostic apparatus. The mobile vehicle includes a wheeled base, a carriage on the base, a hydraulic cylinder for raising and lowering the carriage relative to the base, a load supporting cradle slidably mounted on the carriage for movement in a longitudinal direction between an operative extended position and an inoperative retracted position on the carriage, and a hydraulic system for controlling the operation of the vehicle and its components. The vehicle includes co-operating members on the base and on the docking structure for properly aligning and positioning the vehicle with respect to the docking structure. The movement of the carriage may be accomplished either manually through a foot pump or through a hydraulic power interlock between the vehicle base and docking structure which is engageable upon docking. The carriage, however, may only be lowered if the cradle is in its inoperative position completely on the carriage. A latching mechanism atuomatically locks the vehicle to the docking structure upon docking and may only be unlatched so that the vehicle may be undocked if the cradle is in its inoperative position completely on the carriage. The latching mechanism also automatically actuates a cradle release mechanism so that the cradle may be slid on the carriage. A second cradle locking mechanism is also provided which may only be unlocked when the carriage has been raised to the proper height with respect to the docking structure.

15 Claims, 10 Drawing Figures

HYDRAULIC SYSTEM FOR A MOBILE TRANSPORT VEHICLE THAT SUPPORTS AND POSITIONS A LOAD RELATIVE TO A DOCKING STRUCTURE

BACKGROUND OF THE INVENTION

The present invention relates to a hydraulic system for a mobile vehicle that supports and positions a load relative to a docking structure, and more particularly to hydraulic control circuitry for a patient transport that supports and positions a patient relative to a medical diagnostic apparatus such as a nuclear magnetic resonance machine.

Various types of patient supporting and positioning apparatus are known in the medical industry. For example, apparatus such as patient beds, stretchers, surgical tables and examination tables are commonly employed. Such apparatus usually are constructed with an articulated structure, and may include various drive mechanisms for elevating and tilting either the entire patient or only a specific portion or limb of the patient, such as to provide a backrest or kneelift. The apparatus thus properly positions a patient or a part of the patient's body for treatment and/or examination by a physician or a medical diagnostic apparatus such as an ultra-sound scanner.

One known apparatus used with radiation/oncology treatment linear accelerator machines includes a stationary base located adjacent the radiation ports of the machine, a table that may be raised or lowered with respect to the base, and a cradle slidably mounted for longitudinal movement on the table. A patient to be treated is first transferred from a gurney onto the cradle, and is then lifted to the approximate treatment height by raising the table. The patient and cradle are next slid outwardly from the table so that the body area to be treated is positioned beneath the radiation ports of the machine. The table is then raised or lowered to provide the appropriate height for treatment.

A relatively recent development in medical diagnostic apparatus is the nuclear magnetic resonance machine or NMR machine. An NMR machine employs a large magnet which scans the desired portions of a patient's body to provide images on a screen for diagnostic purposes. A patient must be placed within the interior of an annular magnet in order for scanning to occur. Therefore, a vehicle which transports a patient to the NMR machine must be capable of precisely positioning a patient relative to this annulus.

Various other unique problems are assocated with NMR machines. In operation, an NMR machine will create an extremely strong magnetic field, and thus only non-ferrous equipment may be employed near the machine. Further, any electronic power sources or electronic controls which are employed either with an NMR machine or a patient transport must be remotely located so that the magnetic field does not effect their operation. Thus, known patient handling equipment, which generally employs ferrous materials and electronic power sources and controls for positioning a patient, cannot be used with NMR machines. Additionally, present life support equipment also employs electronic controls and equipment and therefore must also be remotely located from an NMR machine. As a result, the ability to rapidly disengage a critically ill patient from an NMR machine and remove the patient from the scan room must be provided by the patient transport so that the patient may be quickly attached to such life support equipment in an emergency.

SUMMARY OF THE INVENTION

A hydraulic system for a mobile transport vehicle that supports and positions a load relative to a docking structure. The hydraulic system is particularly suitable for use with a vehicle such as a patient transport to support and position a patient relative to a medical diagnostic apparatus.

The mobile vehicle includes a base supported for translational movement relative to a surface, a carriage on the base, moving means for moving the carriage relative to the base, a load-supporting cradle slidably mounted on the carriage for movement in a longitudinal direction between an operative extended position and an inoperative retracted position on the carriage, and a hydraulic system for controlling the operation of the vehicle and its components. When used with an apparatus such as an NMR machine, the cradle's operative position is located within the annulus of the machine. The base preferably is mounted on a plurality of wheels that provide the translational movement. The hydraulic system includes a hydraulic cylinder for providing movement of the carriage relative to the base, as well as cradle release and locking mechanisms for controlling movement of the cradle relative to the carriage.

The vehicle also includes location means on the base for cooperating with guide means on a docking structure to locate and align the vehicle base at a predetermined position with respect to the docking structure. When used with a diagnostic apparatus such as an NMR machine, the locating means properly positions the vehicle and patient relative to the annulus of the machine.

The movement of the carriage may be accomplished either manually or with power assist. The manual means includes a pump mounted on the base which is operable through a foot pedal. The power assist may be provided through a power interlock between the vehicle base and docking structure which is engageable upon docking. More specifically, the interlock includes a male coupler on the drive shaft of a hydraulic motor located in the docking stucture of NMR machine which engages a female coupler on the drive shaft of a hydraulic pump located on the vehicle base to drive the pump and raise or lower the carriage. The carriage, however, may only be lowered if the cradle is in its inoperative position completely on the carriage.

Latching means on the base is also provided for securely locking the base to the docking structure. The latching means automatically locks the base to the docking structure upon docking and may be quickly released by means of a foot pedal. The latching means however, may only be released, and the vehicle undocked if the cradle is in its inoperative position completely on the carriage.

A cradle release mechanism prevents sliding movement of the cradle when the cradle is in its inoperative retracted position. The cradle may only be released in response to latching of the latching means upon docking which indicates that the vehicle is properly located with respect to the docking structure. As a further safety precaution, a second cradle locking mechanism is employed to normally lock the cradle in its inoperative position. This mechanism may only be unlocked when the carriage has been moved to a predetermined desired location with respect to the docking structure, as for example when the carriage is located at the proper height with respect to the annulus of an NMR machine.

The present invention thus provides a hydraulic system for a mobile vehicle that precisely positions a load relative to a docking structure, such as a patient relative to a medical diagnostic apparatus, and also provides the ability to safely and rapidly disengage and disembark from such a docking structure.

BRIEF DESCRIPTION OF THE DRAWINGS

The drawings illustrate the best mode presently contemplated of carrying out the invention.

In the drawings.

DESCRIPTION OF THE PREFERRED EMBODIMENT

Figure 1:
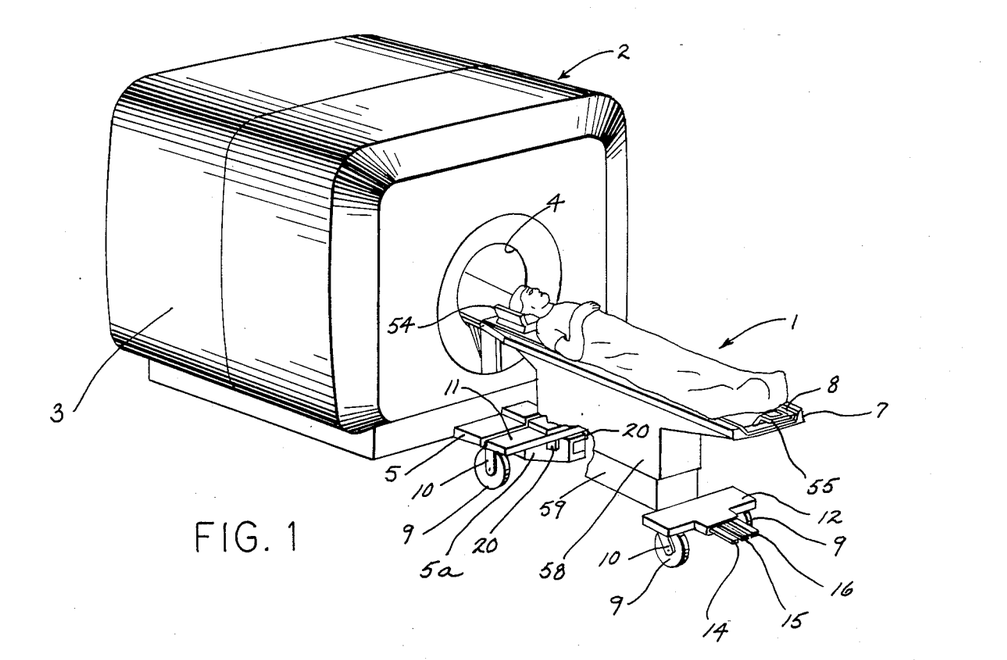
FIG. 1 is a perspective view with parts broken away illustrating a patient transport docked at the entrance to an NMR machine.

Referring now to the drawings, FIG. 1 illustrates a patient transport generally designated by the numeral 1 for supporting and positioning a patient relative to a medical diagnostic apparatus 2 such as a nuclear magnetic resonance or NMR machine. The NMR machine 2 includes an outer enclosure 3 housing a magnet that delivers images of specific portions of a patient's body for diagnostic purposes. The patient is received within an opening or annulus 4 formed in machine 2 during the scanning procedure. Machine 2 also includes a housing 5 located on its front face beneath annulus 4. Housing 5 encloses a hydraulic motor and latching mechanism for cooperation with patient transport 1 in a manner hereinafter to be described. A lower portion 5a of housing 5 contains the latching mechanism, and is V-shaped with its leading edge projecting outwardly from the front face of enclosure 3. Its outer side surfaces are thus tapered and act as a guiding mechanism for cooperation with transport 1 to properly position transport 1 relative to annulus 4, as will hereinafter be described.

Although FIG. 1 illustrates transport 1 as supporting and positioning a patient relative to the NMR machine 2, it is readily apparent that transport 1 is a mobile vehicle that may be employed for supporting and positioning other loads relative to a docking structure. Thus, mobile transport 1 may be employed with other docking structures in various types of applications.

Transport 1 includes a base 6, a carriage 7 movably mounted on base 6, and a patient or load supporting cradle 8 mounted on carriage 7. Base 6 is supported for translational movement over a surface by means of four wheels 9. Wheels 9 are each mounted on casters 10 to provide maneuverability for transport 1. Two of the wheels 9 are affixed to a front cross member 11 while the other two wheels 9 are affixed to a rear cross member 12. Cross members 11 and 12 are mounted to base 6 at opposite ends thereof and extend transversely of the longitudinal direction of base 6. Rear member 12 also mounts three foot pedals 14–16. Foot pedal 14 is employed to manually lower carriage 7 with respect to base 6 while pedal 15 is employed to manually raise carriage 7 with respect to base 6. Foot pedal 16 is employed to unlatch transport 1 from machine 2 so that transport 1 may be undocked therefrom. The operation of foot pedals 14–16 will further be described in connection with FIGS. 3 and 3A herein.

Front cross member 11 includes a pair of spaced apart locating arms 20 depending therefrom. Arms 20 are spaced apart a distance approximately equal to the width of the lower portion of housing 5 on machine 2. If transport 1 is not properly aligned with annulus 4 upon docking one or both of the arms 20 will engage a tapered outer surface of housing 5 and slide along the surface as transport 1 is forced toward annulus 4 until transport 1 is properly aligned with annulus 4, as shown best in FIG. 1. Transport 1 is properly located and aligned with respect to annulus 4 when its longitudinal direction is substantially parallel to the longitudinal axis of annulus 4.

Figure 4:
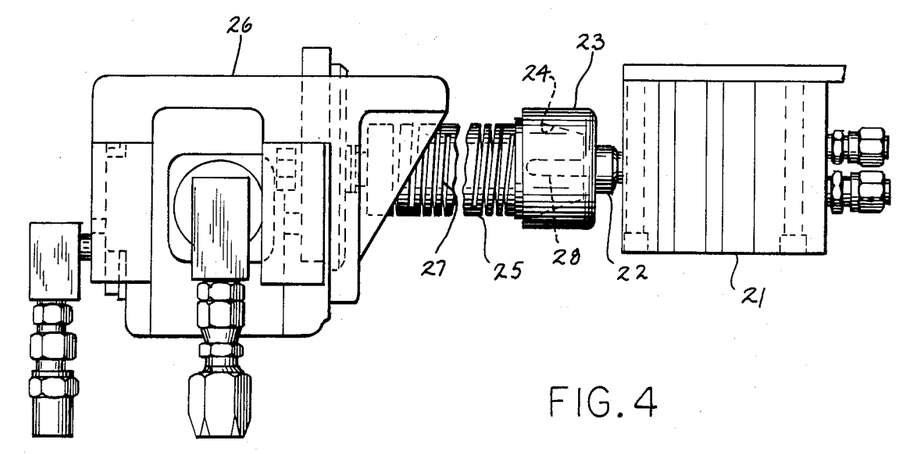
FIG. 4 is an enlarged detail view showing the components of the power interlock between the transport and the NMR machine for raising and lowering a patient on the transport.

Referring now to FIG. 4, cross member 11 also houses a hydraulic pump 21. Pump 21 is of the fixed displacement, reversible type having a shaft 22 with a female clutch or coupler 23 at the end of shaft 22. Clutch 23 includes a tapered annular inner surface 24 for engagement with the outer surface of a male coupler member 25 which in turn is connected to the shaft of a hydraulic motor 26 located within housing 5 of machine 2. Male coupler member 25 includes a continuous spiral slot 27 formed therein which permits coupler 25 to be compressed along its axis and to flex horizontally and vertically so that proper engagement may occur between its head and clutch 23. Clutch 23 includes a finger 28 which is inserted within a corresponding bore in the head of coupler 25 to straighten coupler 25 for proper engagement as transport 1 is docked against machine 2.

Figure 5:
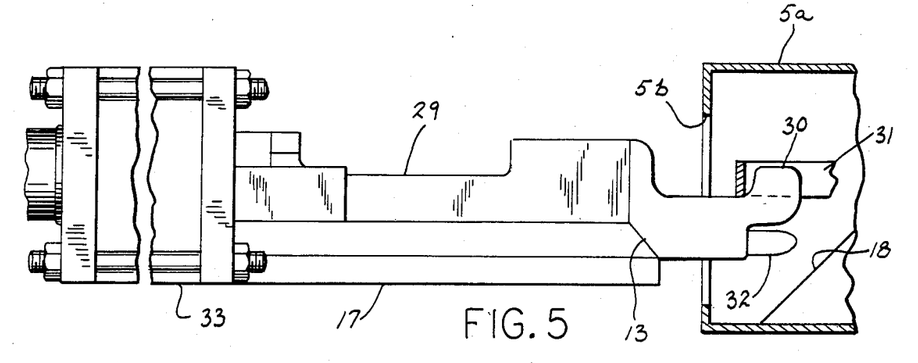
FIG. 5 is an enlarged detail view showing the latch for securing the transport to the NMR machine.

Base 6 also includes a latching means for securely locking transport 1 to machine 2 upon docking. The latching means extends from the front of base 6 and as shown in FIG. 5 includes a spring loaded arm 29 having a hook 30 at its outer end. Arm 29 is biased by its spring inwardly or to the left in FIG. 5. When engaged hook 30 projects through an opening 5b formed in housing portion 5a, and is engageable with a corresponding catch member 31 within housing 5a of machine 2. Arm 29 also includes a button member 32 beneath hook 30 at its outer end, and a cam surface 13 located intermediate its ends which coacts with an abutment member 17 on base 6 to latch and unlatch hook 30. Arm 29 is shown in FIG. 5 in its latched position. In order to unlatch hook 30, hydraulic pressure forces arm 29 outwardly or to the right in FIG. 5 so that cam surface 13 slides on abutment member 17 and hook 30 correspondingly moves downwardly and forwardly until its upper edge clears the lower edge of catch member 31. Transport 1 thus is released from machine 2, and may then be pulled away from machine 2 if cradle 8 is in its inoperative position completely on carriage 7, a will hereinafter be described. To latch hook 30, transport 1 is pushed toward machine 2 so that button member 32 engages a ramp 18 within housing portion 5a. As transport 1 continues to move forwardly, ramp 18 forces button member 32 and arm 29 upwardly until cam surface 13 clears the outer end of abutment member 17 at which time the internal spring of arm 29 forces arm 29 to the left so that hook 30 engages catch member 31 to latch transport 1 on machine 2. Arm 29 is mechanically linked to a three position control valve 33 which controls the flow of hydraulic fluid to a cradle latch release cylinder 34, the operation of which will hereinafter be described.

Figure 2:
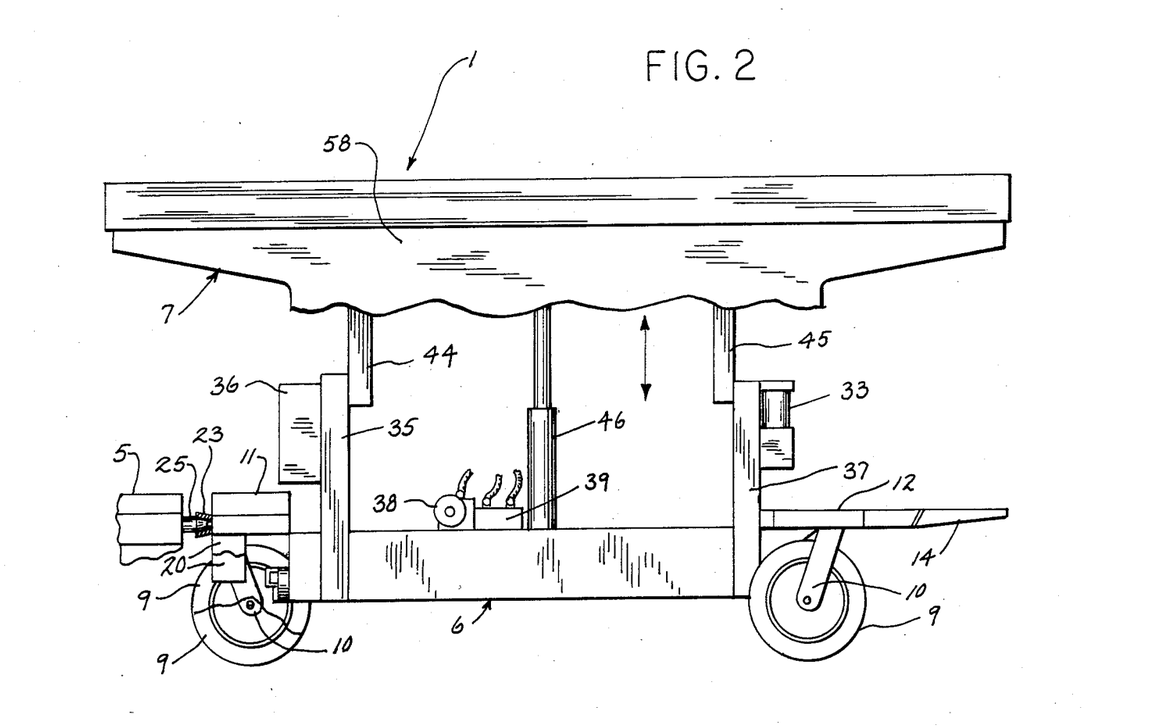
FIG. 2 is a side view in elevation of the patient transport of FIG. 1 with its shroud broken away to show its interior and illustrating a power interlock between the transport and NMR machine.

Base 6 further includes an upright member 35 at its forward end for supporting a hydraulic fluid reservoir 36. Base 6 also includes a second upright member 37 extending upwardly from the rear thereof adjacent foot pedals 14-16. Member 37 functions as a support for mounting a latch release valve 33, the function of which will hereinafter be described. Base 6 also mounts an accumulator assembly 38 and a fluid manifold 39 (see FIGS. 2 and 3A), the function of which will hereinafter be described.

Figures 7, 8:
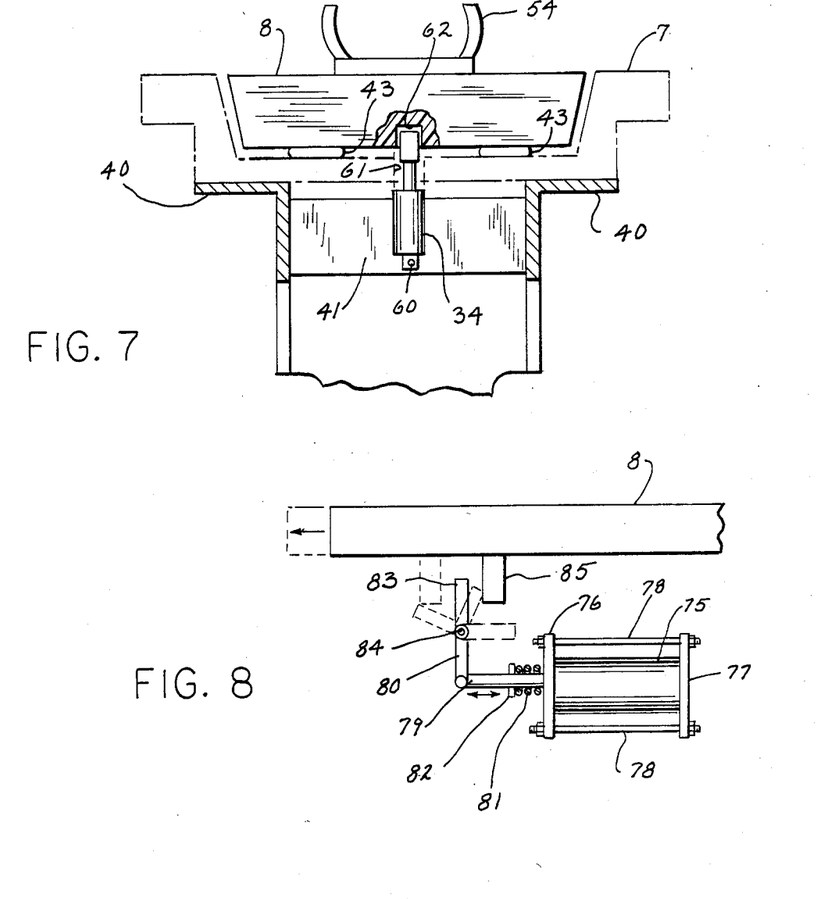
FIG. 7 is a fragmentary end view partially in section and with parts broken away illustrating a cradle release mechanism.
FIG. 8 is a schematic view illustrating the operation of a cradle position indicating mechanism.

Carriage 7 is substantially U-shaped and is supported by a pair of spaced apart L-shaped runner members 40, as shown best in FIG. 7, which extend parallel to one another and in a longitudinal direction from the front to the rear of transport 1. As shown best in FIG. 7, runners 40 are interconnected by a series of brackets 41 which are used not only to maintain proper spacing for runners 40 but also to house various components of transport 1. As shown best in FIG. 7, the base of carriage 7 is supported on runners 40. Cradle 8 is slidably mounted within carriage 7 on a pair of longitudinal bearings 43 formed of a self-lubricating plastic material such as that available under the trade designation "Delrin". Bearings 43, however, could also be formed of conventional plastic rollers mounted in either carriage 7 or cradle 8, or any other non-ferrous bearing arrangement suitable to permit the sliding of cradle 8 with respect to carriage 7. Carriage 7 also includes a forward guide member 44 and a rearward guide member 45 extending between runners 40 and projecting downwardly therefrom. Guide member 44 travels inside of upright member 35 while guide member 45 travels inside of upright member 37. Both members 44 and 45 act as guides for carriage 7 as it moves upwardly and downwardly with respect to base 6. When carriage 7 is in its lowest position, the lower end of guide members 44 and 45 rest on base 6. As a means for moving carriage 7 upwardly and downwardly with respect to base 6, a hydraulic lift cylinder 46 has its cylinder end mounted to base 6 and its rod end to carriage 7.

As shown best in FIGS. 1 and 7, cradle 8 includes a headrest 54 at its forward end and a handle or pull bar 55 at its rearward end. Also, a carriage shroud 58 is attachable to carriage 7, and a base shroud 59 is attachable to base 6. Shrouds 58 and 59 are for esthetic reasons and also function to enclose and protect the components of transport 1.

Referring now to FIG. 7, there is shown a cradle release mechanism which is actuated upon the latching of hook 30 to member 31. The cradle release mechanism includes cradle latch release cylinder 34 which is spring biased to a normally extended position, and is mounted at its cylinder end 60 to bracket 41. The rod end of cylinder 34 projects upwardly through an opening 61 in the base of carriage 7 and into a blind bore 62 in the bottom of cradle 8. In this normally engaged position, cylinder 34 holds cradle 8 in its inoperative position completely on carriage 7 so that it cannot be slid thereon. This extended or engaged position occurs whenever transport 1 is disengaged or undocked from machine 2 so that hook 30 of the latching mechanism is unlatched. However, upon docking arm 29 moves control valve 33 to a position whereby fluid retracts cylinder 34. Cradle 8 may then be slid on carriage 7 assuming that carriage 7 is at the appropriate height, as will hereinafter be described. Upon undocking or unlatching of hook 30, cylinder 34 returns to its extended or engaged position to prevent movement of cradle 8.

Referring now to FIG. 8, there is shown a table position valve 75 mounted to carriage 7 between runners 40 beneath cradle 8. Table position valve 75 is a two-position spring returned shuttle valve and is mounted to one of the runners 40 by a bracket 76 which also serves as an end plate for the valve block. The other end of valve 75 is closed off by a second end plate 77 which is rigidly secured to bracket 76 by a plurality of mounted bolts 78. The spool of valve 75 is connected to a rod 79 projecting through bracket 76 and pivotally connected at its outer end to the lower end of a lever 80. A spring 81 extends between bracket 76 and a flange 82 on rod 79 to normally bias rod 79 to a closed position, i.e. outwardly or to the left as shown in FIG. 8. The upper end of lever 80 is fixedly mounted to an L-shaped paddle member 83 which in turn is pivotally mounted to runner 40, as at 84. Cradle 8 includes an abutment member 85 depending from its underside. Member 85 projects downwardly a sufficient distance so that it will engage and pivot paddle member 83 as cradle 8 is slid on carriage 7. Paddle member 83 is located at the rearward edge of carriage 7 so that valve 75 acts as a cradle position indicator. In other words, when cradle 8 is retracted so that it is completely on carriage 7 member 85 hits paddle member 83 and rotates it to its position shown in broken lines which in turn moves rod 79 inwardly to actuate valve 75 to an open position against spring 81. However, when cradle 8 is slid to an extended position i.e. to the right in FIG. 8 spring 81 forces rod 79 to the left which in turn pivots paddle member 83 to the closed position shown in solid lines in FIG. 8. As will be described, the position of rod 79 and consequently the position of the spool of valve 75 acts as a safety mechanism during the operation of the hydraulic circuitry hereinafter to be described.

Figure 9:
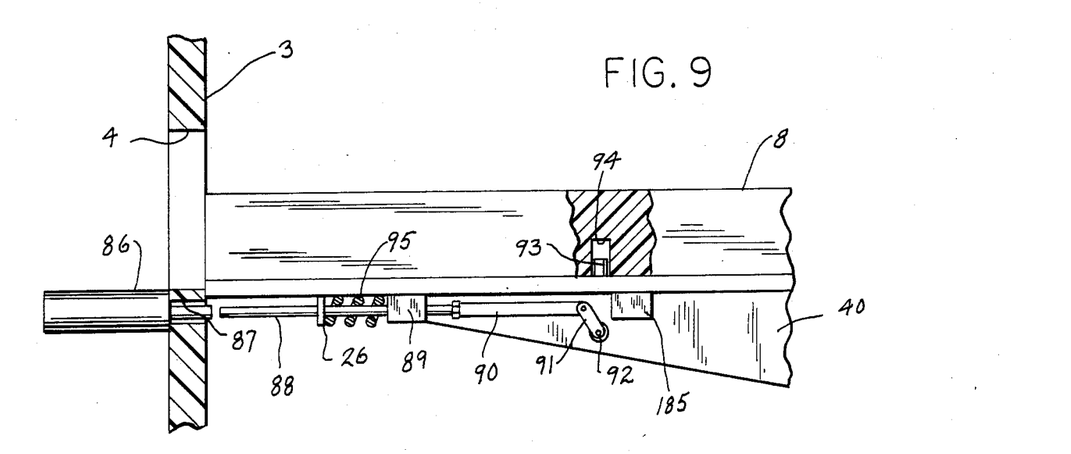
FIG. 9 is an enlarged fragmentary view with parts broken away illustrating a cradle locking mechanism.

Referring now to FIG. 9, there is shown a second cradle locking mechanism which normally locks cradle 8 in its inoperative position. This mechanism functions to unlock cradle 8 to permit sliding movement thereof when carriage 7 has been located at the proper height with respect to annulus 4 of NMR machine 2. As shown, a cylinder 86 is mounted to NMR machine 2 so that its rod extends through an opening 86 formed in outer enclosure 3 beneath annulus 4. The rod of cylinder 86 is positioned to extend horizontally to engage the outer end of an elongate rod 88 which is mounted for sliding movement along its longitudinal axis by a bracket 89 mounted to runner 40. The inner end of rod 88 is threaded into the outer end of a second rod 90 which in turn has its inner end pivotally mounted to the upper end of a link 91. The lower end of link 91 is affixed to a shaft 92 extending between and journalled in runners 40. A cam member (not shown) on shaft 92 engages a pin 93 that rides in a bore 94 formed in cradle 9. A block 185 affixed to runner 40 acts as a stop to limit the rotation of link 91 and shaft 92. A spring 95 surrounds rod 88 and extends between bracket 89 and a flange 96 formed on rod 88. Spring 95 normally biases rod 88 to the position shown in FIG. 9 so that pin 93 extends into bore 94 to prevent the movement of cradle 8. However, when carriage 7 has been raised to the appropriate height with respect to annulus 4 so that cradle 88 is in the proper position for entering annulus 4 and rod 88 is horizontally aligned with the rod of cylinder 86, cylinder 86 may be extended to move rod 88 against the force of spring 95 to rotate link 91 and shaft 92 clockwise as shown in FIG. 9 to permit pin 93 to move downwardly out of bore 94. Once pin 93 is removed from bore 94 cradle 8 may be slid longitudinally on carriage 7 so that it may be moved within annulus 4 of machine 2.

Figure 3:
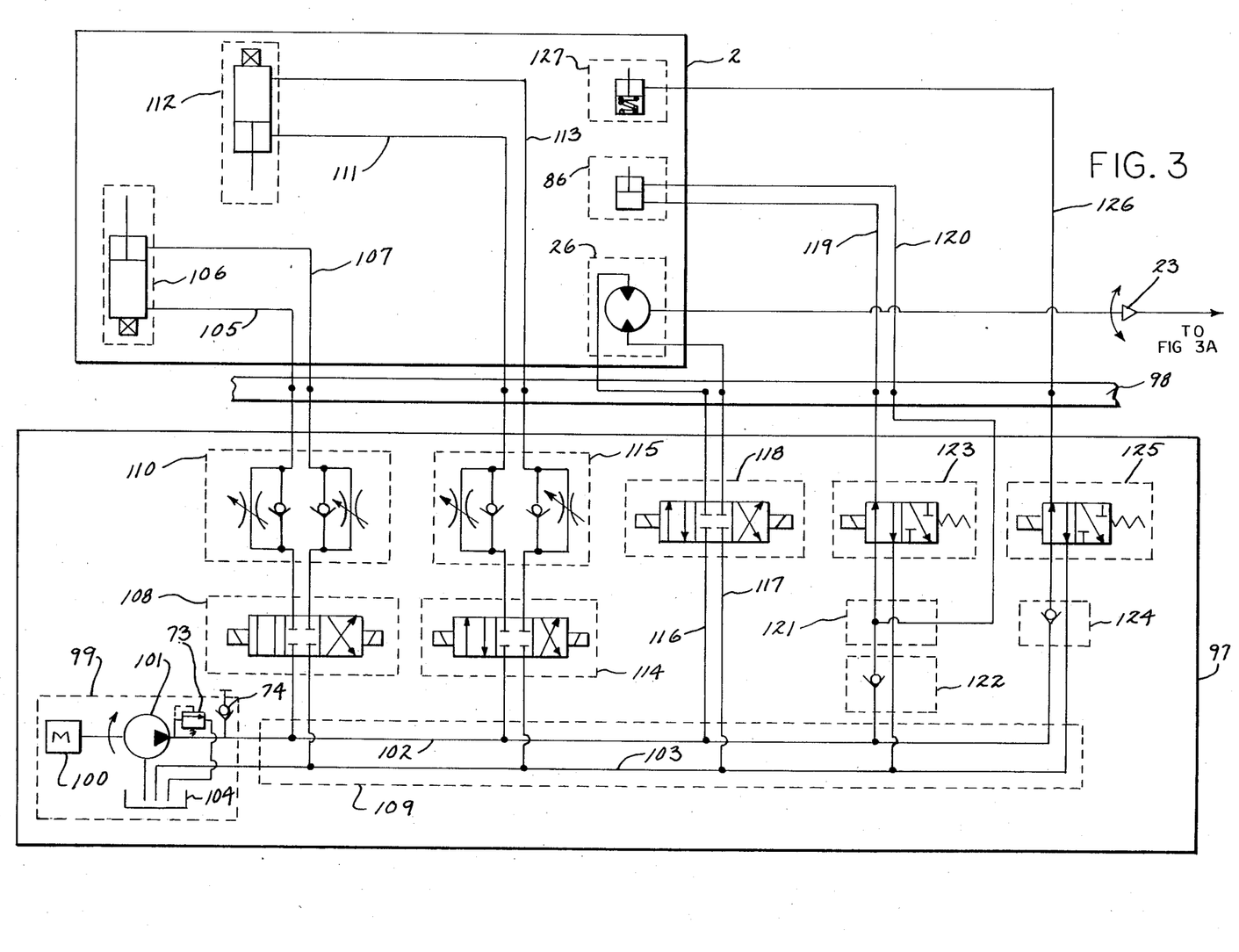
FIGS. 3 and 3A are schematic views illustrating the hydraulic circuitry for the transport of FIG. 2.

Referring now to FIG. 3, the numeral 97 designates an operator's console which is located at a remote location from NMR machine 2. Console 97 may be located in a control room separate from the scanning room which contains NMR machine 2, and this is schematically represented in FIG. 3 by wall 98. Console 97 includes a main pump and motor assembly 99 including a one horsepower A.C. motor 100, a fixed displacement non-reversable pump 101, a pressure relief valve 73 and an air bleed 74. The outlet of pump 101 communicates with a main feed line 102, and a main return line 103 communicates with a reservoir 104. Feed line 102 and return line 103 are contained within a common manifold 109. Feed line 102 communicates with a hydraulic line 105 leading to one side of a double-acting laser positioning cylinder 106 locatd within machine 2. The other side of cylinder 106 communicates via line 107 with return line 103. Cylinder 106 functions to move a laser alignment light to an appropriate mark on a patient so that a patient may be positioned precisely at the required location necessary for scanning the desired body component by NMR machine 2. A solenoid operated, three-position, 4-way control valve 108 is located in the operator's console 97 to control the direction of fluid to and from cylinder 106. Fluid flow in lines 105 and 107 is controlled by a flow control valve 110 located beween valve 108 and cylinder 106. Flow control valve 110 is of the non-compensated type that includes a variable restriction and a check valve for each of the lines 105 and 107.

Feed line 102 also communicates with a hydraulic line 111 leading to one end of a second laser positioning cylinder 112. The other end of cylinder 112 communicates via line 113 to main return line 103. A solenoid operated, three-position, four-way control valve 114 is located in console 97 and controls the direction of fluid flow to and from cylinder 112. A flow control valve 115 identical to control valve 110 controls fluid flow between valve 114 and cylinder 112.

Feed line 102 also communicates with a hydraulic line 116 which leads to one side of a fixed displacement, reversible motor 26 (see FIG. 4). Another line 117 communicates between the other side of motor 26 and main return line 103. A solenoid operated, three position, 4-way control valve 118 located in console 97 controls the direction of fluid flow to and from motor 26.

Main feed line 102 also communicates with a hydraulic line 119 which leads to one side of double-acting cylinder 86 (see FIG. 9). The other side of cylinder 86 communciates via line 120 with a regenerative valve 121. A check valve 122 is disposed in line 119 between valve 121 and main feed line 102. Another hydraulic line 123 communicates between main return line 103 and a solenoid operated, spring-returned, two-position, directional control valve 123 located in console 97. Valve 123 controls the direction of fluid flow between lines 102 and 103 and cylinder 86 to extend or retract cylinder 86.

Main feed line 102 also leads through a check valve 124 to a solenoid operated, spring returned, two-position, directional control valve 125 located in console 97. A hydraulic line 126 in turn communicates between valve 125 and a single acting spring returned cradle latch cylinder 127 located in NMR machine 2. The rod end of cylinder 127 acts in a manner similar to pin 93 (see FIG. 9) to maintain the position of cradle 8 within annulus 4 of machine 2 when a patient is being scanned within machine 2. Cylinder 127 thus prevents any sliding movement of cradle 8 once it is properly positioned within machine 2.

Figure 3A:
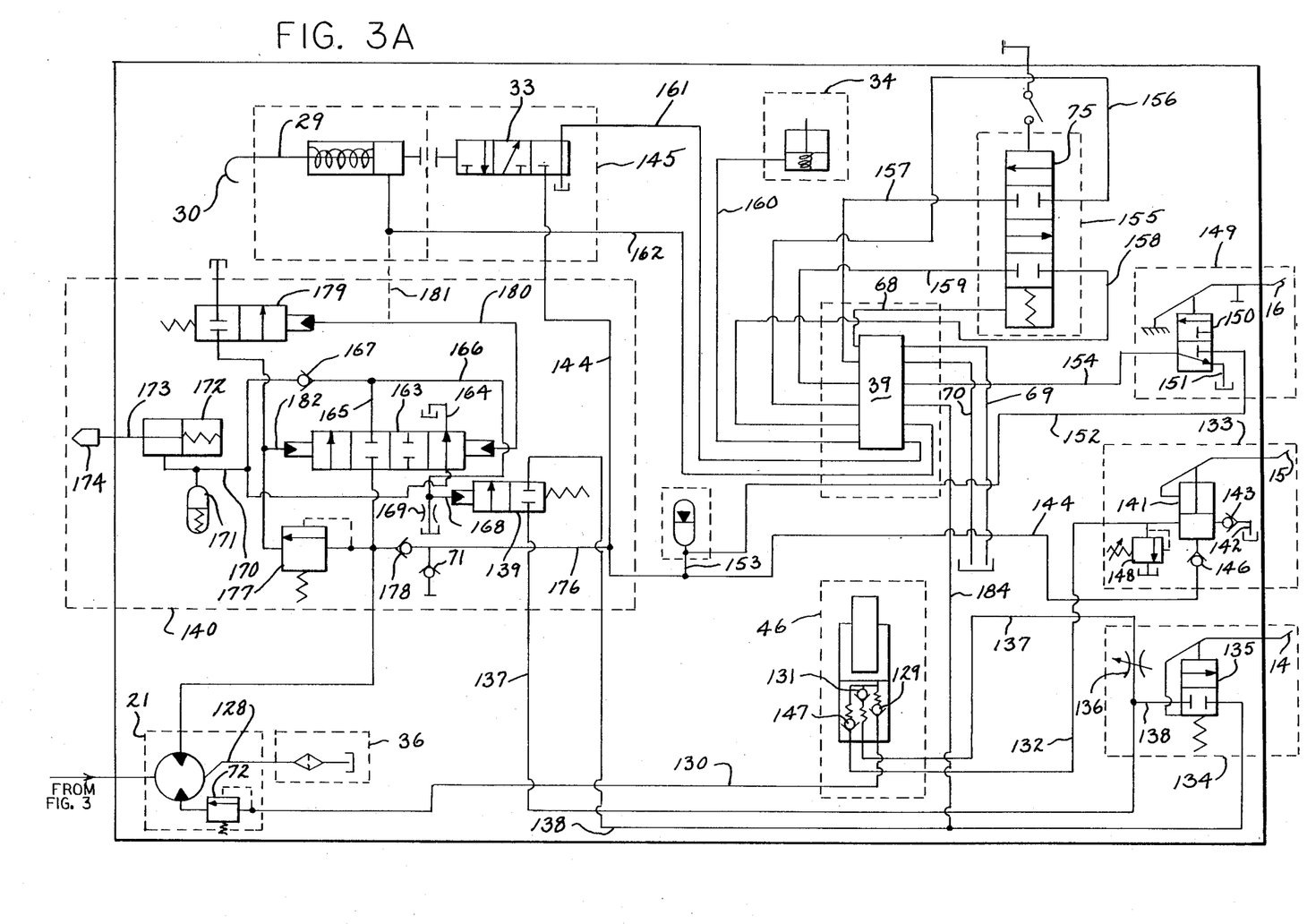

The output shaft of motor 26 engages via male coupler 25 (see FIG. 4) female coupler or clutch 23 which, referring now to FIG. 3A, drives the fixed displacement, reversible pump 21 located in transport 1. Transport 1 is schematically illustrated by the enclosing box of FIG. 3A. Reservoir 36 is illustrated adjacent pump 21, and communicates with pump 21 via line 128. Lift cylinder 46 includes an integral check valve 129 and communicates with pump 28 via hydraulic line 130. A relief valve 72 is disposed between lines 128 and 130. Cylinder 46 includes a second integral check valve 131 disposed in a hydralic line 137 communicating with foot pump assembly 134.

Cradle down valve assembly 134 includes foot pedal 14 which is mechanically linked to a spring-returned two position, two-way control valve 135, and a variable restriction 136 disposed in hydraulic line 137. Valve 135 is disposed in line 138 which communicates between line 137 and a pilot operated, spring-returned, two-position, two-way control valve 139 located in an accummulator monitor valve assembly 140 for controlling the flow of fluid in lines 137 and 138. A line 184 communicates between lines 138 and manifold 39.

Foot pump assembly 133 includes a foot pedal 15 mechanically linked to a piston of a manually actuatable pump 141. Pump 141 communciates via line 142 with tank, and a check valve 143 disposed in line 142 functions to permit the drawings of fluid from tank into pump 141 in the normal manner. Another hydraulic line 144 communicates between pump 141 and three position control valve 33 disposed in latch assembly 145 (see FIG. 5). A check valve 146 is disposed in line 144 to permit fluid flow only in one direction from pump 141 to valve 33. Line 132 communicates with pump 141, and leads to an integral check valve 147 in cylinder 46 to permit fluid flow only from pump 141 to cylinder 46, but not in the reverse direction. A pilot operated pressure relief valve 148 is also disposed in line 132 between check valve 147 and pump 141.

An undocking or latch release assembly 149 includes foot pedal 16 linked to a two-position control valve 150. A hydraulic line 151 communicates between valve 150 and tank, and another hydraulic line 152 communicates between valve 150 and inlet line 153 leading to fluid charged accummulator 38. Another hydraulic line 154 communicates between valve 150 and manifold 39.

Cradle position indicating valve assembly 155 includes cradle position indicator valve 75 shown in FIG. 8 and schematically illustrated in FIG. 3A. Valve 75 is normally biased closed by spring 81. Rod 79 and paddle member 83 are also schematically illustrated in FIG. 3A for moving valve 75 against the force of spring 81 so that when cradle 8 is in its extended position, valve 75 is closed, and when in its retracted position valve 75 is open. A hydraulic line 156 communicates between valve 75 and manifold 39 while another line 157 also communicates between the other side of valve 75 and manifold 39. A third line 158 and a fourth line 159 also communicate between valve 75 and manifold 39. A hydraulic line 68 communicates between the spring chamber of valve 75 and manifold 39 while another line 69 leads from the other side of manifold 39 to tank. Line 70 leads from the side of manifold 39 opposite line 157 to tank.

Cradle release cylinder 34 is schematically illustrated in FIG. 3A as a single-acting spring-returned cylinder. Cylinder 34 communicates via line 160 with manifold 39, and a line 161 leads from manifold 39 to control valve 33. Another hydraulic line 162 communicates between manifold 39 and cradle latch release cylinder 34.

Figure 6:
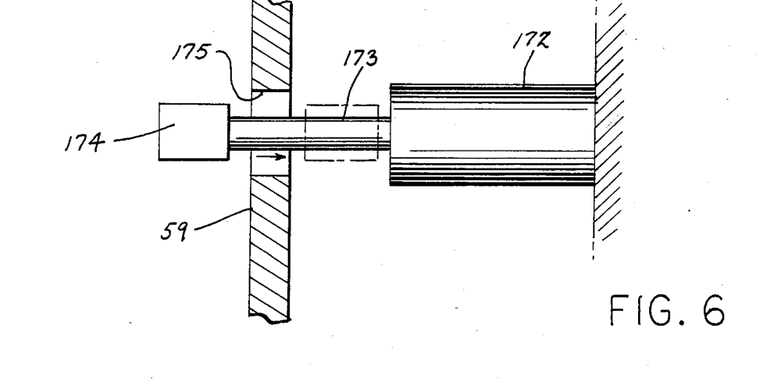
FIG. 6 is an enlarged schematic view showing a flag mechanism for signaling that the hydraulic circuitry is ready for operation.

Besides including valve 139, accummulator monitor valve assembly 140 also includes a solenoid operated three-position directional control valve 163 which has a hydraulic line 164 leading to tank. A hydraulic line 165 communicates between a central closed port of a valve 163 and another hydraulic line 166 which in turn communicates between tank and another port of valve 163. A check valve 167 is disposed in line 166 and a pilot line 168 communicates between line 166 and valve 139. A flow restriction 169 is located in line 166 between its connection with line 168 and tank. Line 166 also communicates via line 170 with a spring-loaded accummulator 171 and a single-acting spring-returned cylinder 172 (see FIG. 6). Cylinder 172 includes a rod 173 having a flag or signal member 174 at its outer end which extends and retracts through an opening 175 formed in shroud 59 of base 6. Thus, flag member 174 normally projects outside of shroud 59, and moves inwardly (i.e., to the right in FIG. 6), to be hidden from sight upon actuation of cylinder 172. Flag member 174 functions as an indicator to an operator that the hydraulic system shown in FIGS. 3 and 3A have reached a condition having sufficient pressure for operation. In other words, when flag member 174 disappears from sight, an operator knows that the transport 1 is operational and ready to proceed as will hereinafter be described.

The accummulator monitor valve assembly 140 also includes a hydraulic line 176 communicating between line 144 and tank. A pilot operated pressure relief valve 177 is disposed in line 176 with a check valve 178 located between valve 177 and line 144. An air bleed 71 is also located in line 176 between check valve 178 and line 144. A pilot operated, spring-returned, two-position 2-way control valve 179 is also disposed in line 176 between pressure relief valve 177 and tank. As shown in FIG. 3A, valve 179 is normally closed but may be actuated to an open position by pressure in line 180. Line 180 communicates between valve 179 and the right hand side of valve 163, and also communicates with line 162 via a pilot line 181. A line 182 communicates between line 176 in the left hand side of valve 163 for actuating valve 163 to the right as shown in FIG. 3A.

Finally, a line 183 communicates between the other side of pump 21, line 176 and valve 163.

The operation of patient transport 1 will now be described. It should intially be assumed that a patient is positioned on cradle 8 and transport 1 is being moved toward annulus 4 of NMR machine 2. As transport 1 approaches machine 2, locating arms 20 depending from cross member 11 of base 6 engage the tapered surfaces of the lower portion 5a of housing 5 and guide transport 1 to a location that is parallel to the longitudinal axis of annulus 4. As transport 1 is pushed toward machine 2, hook 30 engages or latches with member 31, as previously described herein, which in turn moves sequence or control valve 33 from the position shown in FIG. 3A to a central position which opens communication between lines 144 and 161. Fluid pressure from accumulator 38 then passes to line 144 through valve 33 into line 161 and then through manifold 39 and line 160 to cradle latch release cylinder 34. Cylinder 34 is thus retracted which, as shown in FIG. 7, disengages cradle 8. At the same time, since cradle 8 is in its fully retracted position, cradle position valve 75 is in its open position resulting in lines 162, 158, 159, and 154 being open to tank since valve 150 is in the position shown in FIG. 3A. Thus, at this point, transport 1 is docked and latched to NMR machine 2 with the cradle release mechanism shown in FIG. 7 disengaged from cradle 8. Note that the cradle release mechanism shown in FIG. 7 will only become disengaged from cradle 8 if cradle 8 is in its fully retracted position on carriage 7 since if it is not, cradle position valve 75 will remain in the position shown in FIG. 3A preventing fluid in line 162 from communicating with tank pressure and thus preventing the movement of hook 30 to engage member 31.

After docking and latching, system pressure must be established to insure proper operation. This is accomplished by recharging accummulator 38. Thus, if signal flag 174 on cylinder 172 is in its charge accumulator state, i.e. projecting through opening 175 in shroud 59 (see FIG. 6), valve 118 will be actuated allowing fluid from line 102 to be directed through line 116 to motor 26. Since motor 26 is mechanically linked by coupler 25 and cone clutch 23 to pump 21, motor 26 rotates pump 21 to direct fluid through line 183 and then through lines 176, 144, and 153 to recharge accumulator 138. Proper accummulator pressure should be reached within about 2 to 7 seconds. The desired pressure is regulated by pressure relief valve 177 so that when the setting of valve 177 is reached, valve 177 opens allowing fluid to be directed into line 182 to move valve 163 to the right as shown in FIG. 3A which in turn causes fluid to be directed through lines 165 and 166 past check valve 167 and then through line 170 to cylinder 172 to retract signal flag 174. Signal flag 174 thus presents a visual indication to an operator that full recharge pressure has been reached and that transport 1 is ready for operation.

At substantially the same time, fluid is directed from main supply line 102 through lines 119 and 120 to locking cylinder 86, and through line 126 to cradle latch cylinder 127. Cradle latch cylinder 127 is thus retracted in preparation for receiving cradle 8 within annulus 4 of machine 2. Cylinder 86 is thus also made ready for operation.

Carriage 7 and cradle 8 are now in position to be elevated or raised. The movement of the carriage may be accomplished either manually or with power assist. If it is desired to manually raise the patient, foot pedal 15 is depressed and released causing foot pump 141 to draw fluid from tank past check valve 143 and through line 142. When pedal 15 is depressed a second time, fluid is directed past check valve 147 through line 132 to extend lift cylinder 46. Pedal 15 is then reciprocated by the operator a sufficient number of times to extend cylinder 46 sufficiently to raise carriage 7 and cradle 8 to the desired elevation with respect to annulus 4 of machine 2.

If power assist is desired to raise carriage 7 and cradle 8, valve 118 is actuated to direct fluid to motor 126 which in turn rotates pump 21 to cause fluid to be directed through line 130 to lift cylinder 46. When the proper elevation is reached valve 118 is deactuated.

The next operation is the positioning of the laser lights to insure proper patient location for the scanning study to be performed. This is accomplished by actuating valve 108 to extend or retract laser positioning cylinder 106, and by actuating valve 114 to extend or retract laser positioning cylinder 112. When the laser lights are properly located indicating that the patient is properly aligned for scanning, valves 108 and 114 are deactuated and the patient is ready for scanning.

At this point, valve 123 is actuated to extend cylinder 86 (see FIG. 9) to engage rod 88 and lower pin 93 out of bore 94. This releases cradle 8 from carriage 7 so that cradle 8 may be slid into annulus 4 of machine 2. It should be noted when cylinder 86 is extended, it also acts as a safety mechanism to prevent carriage 7 from dropping should there be some malfunction, such as hydraulic line bursting.

Cradle 8 and the patient thereon may then be moved into annulus 4 of machine 2 for scanning. Cradle 8 may be moved either manually by an operator or travel may be controlled by a hydraulic power unit (not shown) having a patient positioning motor which is actuated in a manner similar to that shown in FIG. 3 with respect to motor 26. Note that when the patient and cradle 8 are moved into annulus 4 of machine 2, abutment member 85 (see FIG. 8) disengages from paddle member 83 and spring 81 causes cradle position valve to return to its closed position as shown in FIG. 3A. Thus, carriage 7 and cradle 8 cannot be raised or lowered, nor can transport 1 be unlatched or undocked from machine 2.

After scanning, the patient in cradle 8 is retracted onto carriage 7 outside of machine 2. When cradle 8 is fully retracted onto carriage 7, paddle member 83 is once again pivoted as shown in FIG. 8 causing cradle position valve 75 to move to its open position to enable carriage 7 and cradle 8 to be lowered and transport 1 to be undocked. First, however, cylinder 86 is retracted by actuating valve 123. As shown in FIG. 9, spring 95 returns rod 88 to its original extended position causing pin 93 to once again be engaged in bore 94 causing cradle 8 to be locked in position.

Carriage 7 and cradle 8 may then be lowered. The lowering movement may be accomplished either manually or with power assist. If it is desired to manually lower the patient, an operator depresses foot pedal 14 which opens valve 135. Lift cylinder 46 then retracts under the weight of the patient, cradle 8 and carriage 7 by allowing fluid to pass through check valve 131, line 137, line 138, line 184, manifold 39, line 156, cradle position valve 75, line 157, manifold 39 and then through line 70 to tank. Note that valve 139 in the accummulator monitor valve assembly 140 is closed at this point in time.

If power assist is desired for lowering the patient, valve 118 is actuated so that fluid from main supply line 102 is directed to motor 26 which in turn rotates pump 21 to direct fluid into line 183. Pressure in line 183 will increase since at this point in time valve 163 is closed and fluid will not flow into line 176 due to check valve 146 in line 144, valve 150 being closed, accummulator 38 being fully charged, and cradle latch release cylinder 34 being previously actuated. When the pressure in line 183 reaches the setting of relief valve 177, relief valve 177 will open directing fluid into line 182 which will actuate valve 163 to the right as shown in FIG. 3A. Fluid from line 183 will then pass through valve 163 into line 165 and then into line 166. Due to orifice 169 fluid will be directed into line 168 to actuate valve 139 to an open position. Once valve 139 is opened, fluid from lift cylinder 46 can be directed through check valve 131, line 137, through valve 139, line 138, line 184, manifold 39, line 156, valve 75, line 157, manifold 39 and then through line 70 to tank. Note that valve 135 in cradle down assembly 134 is closed at this point in time. Fluid thus returns to tank by the weight of the patient, carriage 7, and cradle 8. The rate of descent is controlled by metered orifice 169. After the patient has been lowered to the desired height, valve 118 is deactuated. Again, it should be noted that the patient may only be lowered if cradle 8 is fully retracted on carriage 7 so that valve 75 is open.

Once the patient has been lowered to the desired position, transport 1 may be unlatched or undocked from machine 2. In order to accomplish this, an operator depresses foot pedal 16 which closes line 151 and allows communication between lines 152 and 154. This permits fluid from the charged accummulator 38 to be directed from line 152 through valve 150 and into line 154, and then through manifold 39 into line 159. Since cradle 8 is fully retracted on carriage 7, valve 75 is open which allows fluid to pass therethrough into line 158 and then once again through manifold 39 into line 162 to push hook 30 out and release it from member 31, as previously described herein. When hook 30 is extended, valve 33 moves with it to close line 144 and open line 161 to tank. This permits fluid to drain from cradle latch release cylinder 34 into line 160, through manifold 39 into line 161 and then to tank. As this occurs, the rod end of cylinder 34 once again engages bore 62 locking cradle 8 into its retracted position. At substantially the same time, fluid in line 162 is directed into pilot line 181 and then into line 180 which actuates valve 179 to open line 182 to tank which moves valve 163 to the left to once again block line 183. Transport 1 and the patient may then be undocked from machine 2.

It should be noted that after cradle 8 is removed from annulus 4 of machine 2 valve 125 is deactuated so that line 126 communicates with return line 103 causing cradle latch cylinder 127 to extend and act as a stop preventing any entry of cradle 8 into annulus 4 unless transport 1 is preoperly docked with machine 2.

A mobile vehicle for supporting and positioning a load relative to a docking structure and the hydraulic circuitry for operating said vehicle has been illustrated and described. Specifically, the vehicle has been illustrated and described in connection with a patient transport for supporting and positioning a patient relative to a medical diagnostic apparatus such as an NMR machine. However, various modifications and/or substitutions of the specific components described herein may be made without departing from the scope of the invention. For example, various types of valves, cylinders, motors and pumps may be substituted for those hydraulic components specifically described herein.

Various modes of carrying out the invention are contemplated as being within the scope of the following claims particularly pointing out and distinctly claiming the subject matter which is regarded as the invention.

I claim:

1. A mobile vehicle for supporting and positioning a load relative to a docking structure, comprising:
    a base supported for translational movement over a surface;
    a carriage movably mounted on said base;
    moving means for moving said carriage vertically relative to said base;
    a load-supporting cradle mounted on said carriage for horizontal movement between operative and inoperative positions relative to said carriage;
    hydraulic means on said base including coupling means for cooperating with a docking structure for operatively connecting and driving said moving means to a docking structure to enable actuation of said moving means through said coupling means upon docking;
    latching means on said base actuatable between latched and unlatched positons for releasably securing said base to the docking structure, said latching means actuatable to its latched position only when said cradle is located in its inoperative position;
    cradle release means normally holding said cradle in said inoperative position, and actuatable to a release position in response to said latching means moving to said latched position to release said cradle; and
    cradle locking means independent of said cradle release normally in a locked position locking said cradle in said inoperative position, and actuatable to an unlocked position in response to the movement of said carriage to a desired position with respect to said base.

2. The vehicle of claim 1, wherein said moving means includes a hydraulic cylinder connected between said base and said carriage, and pump means for extending and retracting said cylinder.

3. The vehicle of claim 2, wherein said pump means is directly connected to said coupling means.

4. The vehicle of claim 3, whrein said coupling means includes female means releasably connectable with a docking structure.

5. The vehicle of claim 1, further including locating means on said base for cooperating with guide means on a docking structure to locate said base at a predetermined position relative to a docking structure upon docking.

6. In combination, a mobile vehicle for supporting and positioning a load, said vehicle including a base supported for translational movement over a surface, a carriage movably mounted on said base, a hydraulic system including moving means for moving said carriage relative to said base, said moving means includes lift means for raising and lowering said carriage with respect to said base, a load-supporting cradle mounted on said carriage for horizontal movement between operative and inoperative positions relative to said carriage, locating means on said base, cradle position sensing means for sensing the position of said cradle and preventing the lowering of said carriage by said lift means unless said cradle is in its inoperative position, latching means on said base actuatable between latched and unlatched positions for releasably securing said base to said docking structure, said latching means actuatable to its latched position only when said cradle is located in its inoperative position, and said cradle position sensing means further preventing the actuation of said latching means to its unlatched positon unless said cradle is in its inoperative position, and a docking structure to which said vehicle may be docked, said docking structure including guide means cooperating with said locating means for locating said base at a predetermined lateral position relative to said docking structure, and means on said docking structure for driving the hydraulic system, which, in turn, operates said moving, sensing and latching means.

7. The vehicle of claim 6, further including cradle release means normally holding said cradle in said inoperative position, and actuatable to a release position in response to said latching means moving to said latched position to release said cradle.

8. The combination of claim 6, wherein said lifting means includes a hydraulic cylinder connected between said base and said carriage and pump means for extending and retracting said cylinder.

9. The combination of claim 8, wherein said pump means includes a manually operable pump member for extending said cylinder to raise said carriage having an inlet fluid supply line connected to tank and an outlet fluid discharge line connected to said cylinder.

10. The combination of claim 9, further including a manually operable carriage down valve for lowering said carriage having an inlet fluid supply line connected to said cylinder and an outlet fluid discharge line connected to tank, said carriage down valve being movable between a closed position which prevents lowering of said carriage and an open position which permits lowering of said carriage.

11. The combination of claim 10, wherein said cradle position sensing means includes a cradle position valve disposed in the inlet fluid supply line of said carriage down valve, said cradle position valve being movable between a closed position when said cradle is in its operative position and an open position when said cradle is in its inoperative position.

12. The combination of claim 8, wherein said docking structure further includes hydraulic motor means mounted thereon, said pump means includes a reversible hydraulic pump member mounted on said base having a pair of discharge ports and a hydraulic line interconnecting one of said ports and said lift cylinder, and said interlock means includes a first coupling member operatively connected to said pump member and a second coupling member operatively connected to said motor means so that upon actuation of said motor means said motor means drives said pump member to extend said cylinder and raise said carriage.

13. The combination of claim 12, wherein one of said coupling members includes female means and the other of said coupling members includes male means releasably connectable therewith.

14. The combination of claim 12, further including a pilot operated carriage down valve for lowering said carriage, a second hydraulic line communicating between said carriage down valve and the other discharge port of said pump member, a third hydraulic line communicating between said carriage down valve and said cylinder, and a fourth hydraulic line between said carriage down valve and tank, said carriage down valve movable between a closed position which prevents lowering of said carriage and an open position which permits lowering of said carriage.

15. The combination of claim 6, further including cradle locking means normally in a locked position locking said cradle in its inoperative position, and actuation means on said docking structure for actuating said cradle locking means to an unlocked position when said carriage is moved to a desired position with respect to said base.

* * * * *